(12) United States Patent
Gordon et al.

(10) Patent No.: US 9,764,127 B2
(45) Date of Patent: Sep. 19, 2017

(54) MEDICAL LEAD ANCHORING

(71) Applicant: Cardiac Pacemakers, Inc., St. Paul, MN (US)

(72) Inventors: Jack Gordon, Minneapolis, MN (US); Arthur J. Foster, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 20 days.

(21) Appl. No.: 14/975,678

(22) Filed: Dec. 18, 2015

(65) Prior Publication Data

US 2016/0175581 A1    Jun. 23, 2016

Related U.S. Application Data

(60) Provisional application No. 62/094,905, filed on Dec. 19, 2014.

(51) Int. Cl.
*A61N 1/05* (2006.01)

(52) U.S. Cl.
CPC ............. *A61N 1/05* (2013.01); *A61N 1/0558* (2013.01); *A61N 1/057* (2013.01); *A61N 1/059* (2013.01)

(58) Field of Classification Search
None
See application file for complete search history.

(56) References Cited

U.S. PATENT DOCUMENTS

| | | |
|---|---|---|
| 3,244,147 A | 4/1966 | Ueno et al. |
| 3,244,174 A | 4/1966 | Shadduck et al. |
| 3,474,791 A | 10/1969 | Bentov |
| 3,737,579 A | 6/1973 | Bolduc |
| 4,142,530 A | 3/1979 | Wittkampf |
| 4,161,952 A | 7/1979 | Kinney et al. |
| 4,258,724 A | 3/1981 | Balat et al. |
| 4,341,226 A | 7/1982 | Peters |

(Continued)

FOREIGN PATENT DOCUMENTS

| | | |
|---|---|---|
| DE | 2219044 A1 | 11/1972 |
| DE | 4425195 C1 | 11/1995 |

(Continued)

OTHER PUBLICATIONS

International Search Report and Written Opinion issued in PCT/US2015/066939, dated Mar. 14, 2016, 11 pages.

(Continued)

*Primary Examiner* — Erica Lee
(74) *Attorney, Agent, or Firm* — Faegre Baker Daniels LLP

(57) ABSTRACT

Various embodiments concern a lead system for anchoring a lead, the lead system comprising a lead and an anchor. The anchor can comprise a ring and a flange extending from the ring. The anchor can be mounted on the lead such that the lead extends through the ring and the flange extends over an electrode of the lead. The lead system can further comprise a tether having a proximal portion and a distal portion. The proximal portion of the tether can attached to the lead while the distal portion of the tether can be attached to a needle. During an implantation procedure, the tether can be cut to remove the needle. The tether can then be attached to the flange. The lead, the anchor, and the tether can form a loop around a section of tissue to anchor the lead to the tissue.

17 Claims, 11 Drawing Sheets

(56) References Cited

U.S. PATENT DOCUMENTS

| | | | |
|---|---|---|---|
| 4,355,642 A | 10/1982 | Alferness | |
| 4,378,023 A | 3/1983 | Trabucco | |
| 4,444,206 A | 4/1984 | Gold | |
| 4,444,207 A | 4/1984 | Robicsek | |
| 4,475,560 A | 10/1984 | Tarjan et al. | |
| 4,628,944 A | 12/1986 | MacGregor et al. | |
| 4,633,880 A | 1/1987 | Osypka et al. | |
| 4,735,205 A | 4/1988 | Chachques et al. | |
| 4,827,940 A | 5/1989 | Mayer et al. | |
| 4,991,578 A | 2/1991 | Cohen | |
| 5,009,229 A | 4/1991 | Grandjean et al. | |
| 5,033,477 A | 7/1991 | Chin et al. | |
| 5,217,027 A | 6/1993 | Hermens | |
| 5,241,957 A * | 9/1993 | Camps | A61N 1/0551 607/119 |
| 5,246,014 A | 9/1993 | Williams et al. | |
| 5,300,107 A | 4/1994 | Stokes et al. | |
| 5,314,462 A | 5/1994 | Heil et al. | |
| 5,314,463 A | 5/1994 | Camps et al. | |
| 5,318,543 A | 6/1994 | Ross et al. | |
| 5,327,909 A | 7/1994 | Kiser et al. | |
| 5,336,252 A | 8/1994 | Cohen | |
| 5,350,419 A | 9/1994 | Bendel et al. | |
| 5,385,579 A | 1/1995 | Helland | |
| 5,423,876 A | 6/1995 | Camps et al. | |
| 5,476,500 A | 12/1995 | Fain et al. | |
| 5,492,119 A | 2/1996 | Abrams | |
| 5,693,081 A | 12/1997 | Fain et al. | |
| 5,716,392 A | 2/1998 | Bourgeois et al. | |
| 5,755,767 A | 5/1998 | Doan et al. | |
| 5,807,399 A | 9/1998 | Laske et al. | |
| 5,836,994 A | 11/1998 | Bourgeois | |
| 5,871,532 A | 2/1999 | Schroeppel | |
| 6,041,258 A | 3/2000 | Cigaina et al. | |
| 6,173,206 B1 | 1/2001 | Shchervinsky | |
| 6,304,786 B1 | 10/2001 | Heil, Jr. et al. | |
| 6,360,129 B1 | 3/2002 | Ley et al. | |
| 6,360,130 B1 | 3/2002 | Duysens et al. | |
| 6,370,434 B1 | 4/2002 | Zhang et al. | |
| 6,405,091 B1 | 6/2002 | Vachon et al. | |
| 6,434,431 B1 | 8/2002 | Camps et al. | |
| 6,459,937 B1 | 10/2002 | Morgan et al. | |
| 6,473,654 B1 | 10/2002 | Chinn | |
| 6,491,707 B2 | 12/2002 | Makower et al. | |
| 6,510,332 B1 | 1/2003 | Greenstein | |
| 6,512,958 B1 | 1/2003 | Swoyer et al. | |
| 6,535,764 B2 | 3/2003 | Imran et al. | |
| 6,567,704 B2 | 5/2003 | Sundquist et al. | |
| 6,613,062 B1 | 9/2003 | Leckrone et al. | |
| 6,626,919 B1 | 9/2003 | Swanstrom | |
| 6,671,553 B1 | 12/2003 | Helland et al. | |
| 6,671,561 B1 | 12/2003 | Moaddeb | |
| 6,673,058 B2 | 1/2004 | Snow | |
| 6,752,813 B2 | 6/2004 | Goldfarb et al. | |
| 6,842,648 B2 | 1/2005 | Partridge et al. | |
| 6,934,589 B2 | 8/2005 | Sundquist et al. | |
| 6,941,174 B2 | 9/2005 | Shchervinsky | |
| 6,961,621 B2 | 11/2005 | Krishnan et al. | |
| 7,418,298 B2 | 8/2008 | Shiroff et al. | |
| 7,499,757 B2 | 3/2009 | Coe et al. | |
| 8,868,214 B2 | 10/2014 | Osypka | |
| 2001/0000349 A1 | 4/2001 | Coe et al. | |
| 2001/0039436 A1 | 11/2001 | Frazier et al. | |
| 2002/0013571 A1 | 1/2002 | Goldfarb et al. | |
| 2002/0072787 A1 | 6/2002 | Partridge et al. | |
| 2002/0077685 A1 | 6/2002 | Sundquist et al. | |
| 2002/0123785 A1 | 9/2002 | Zhang et al. | |
| 2002/0165589 A1 | 11/2002 | Imran et al. | |
| 2002/0183818 A1 | 12/2002 | Willilams et al. | |
| 2003/0023295 A1 | 1/2003 | Osypka | |
| 2003/0028232 A1 | 2/2003 | Camps et al. | |
| 2003/0045919 A1 | 3/2003 | Swoyer et al. | |
| 2003/0055463 A1 | 3/2003 | Gordon et al. | |
| 2003/0125787 A1 | 7/2003 | Shchervinsky | |
| 2003/0204231 A1 | 10/2003 | Hine et al. | |
| 2004/0010282 A1 | 1/2004 | Kusleika | |
| 2004/0015193 A1 | 1/2004 | Lamson et al. | |
| 2004/0054388 A1 | 3/2004 | Osypka | |
| 2004/0260371 A1 | 12/2004 | Greenland et al. | |
| 2005/0033394 A1 | 2/2005 | Seifert et al. | |
| 2005/0033395 A1 | 2/2005 | Seifert et al. | |
| 2005/0033396 A1 | 2/2005 | Ospyka | |
| 2005/0070986 A1 | 3/2005 | Tockman et al. | |
| 2005/0113900 A1 | 5/2005 | Shiroff et al. | |
| 2005/0113901 A1 | 5/2005 | Coe et al. | |
| 2005/0137672 A1 | 6/2005 | Coe et al. | |
| 2006/0247752 A1 | 11/2006 | Osypka | |
| 2008/0183257 A1 | 7/2008 | Imran et al. | |
| 2008/0249596 A1 | 10/2008 | Shiroff et al. | |
| 2012/0232626 A1 * | 9/2012 | Daglow | A61M 25/04 607/116 |
| 2013/0338730 A1 | 12/2013 | Shiroff et al. | |

FOREIGN PATENT DOCUMENTS

| | | |
|---|---|---|
| EP | 1000634 A1 | 5/2000 |
| EP | 1025802 A1 | 8/2000 |
| GB | 2025236 A | 1/1980 |
| WO | 9309840 A1 | 5/1993 |
| WO | 2004091716 A1 | 10/2004 |
| WO | 2005028023 A1 | 3/2005 |

OTHER PUBLICATIONS

Agreement between Cardiac Pacemakers, Inc. and Dr. Osypka GmbH, dated Aug. 26, 2002, 2 pp.

Assad et al. New Lead for In-Utero Pacing for Fetal Congenital Heart Block. Journal of Thoracic and Cardiovascular Surgery: 300-302. Jul. 2003.

Epstein et al. Long-Term Performance of Bipolar Epicardial Atrial Pacing Using an Active Fixation Bipolar Endocardial Lead. PACE, 21:1098-1104, Apr. 1998.

European Search Report issued in EP Application No. 10075223, mailed Jul. 28, 2010, 4 pages.

German Office Action citing prior art to related German Patent Application and English translation thereof.

International Search Report and Written Opinion of International Application No. PCT/US2004/010907, filed Apr. 9, 2004, dated Sep. 16, 2004.

International Search Report and Written Opinion of International Application No. PCT/US2004/035172, filed Oct. 22, 2004, both dated Jan. 31, 2005.

Karpawich et al. Improved Epimyocardial Pacing: Initial Experience with a New Bipolar, Steroid-Eluting, High Impedance Lead Design. PACE, 17:2032-2037, Nov. 1994.

Office Action received in related case U.S. Appl. No. 10/821,421, dated Mar. 22, 2007.

Office Action received in related case U.S. Appl. No. 10/821,421, dated May 25, 2006.

Office Action received in related case U.S. Appl. No. 10/821,421, dated Nov. 24, 2006.

Office Action received in related case U.S. Appl. No. 10/971,549, dated Feb. 2, 2007.

Office Action received in related case U.S. Appl. No. 10/971,549, dated Jul. 27, 2007.

Office Action received in related case U.S. Appl. No. 10/971,577, dated Aug. 7, 2007.

Office Action received in related case U.S. Appl. No. 10/972,049, dated Jan. 11, 2007.

Office Action received in related case U.S. Appl. No. 10/972,049, dated Jul. 2, 2007.

Office Action received in related case U.S. Appl. No. 10/972,049, dated Jul. 24, 2006.

Office Action received in related case U.S. Appl. No. 10/972,298; dated Apr. 17, 2007.

(56) References Cited

OTHER PUBLICATIONS

Worley et al. Construction of a Multipolar Electrode System Referenced and Anchored to Endocardium for Study of Arrhythmias. American Physiological Society, H530-H536, 1986.

* cited by examiner

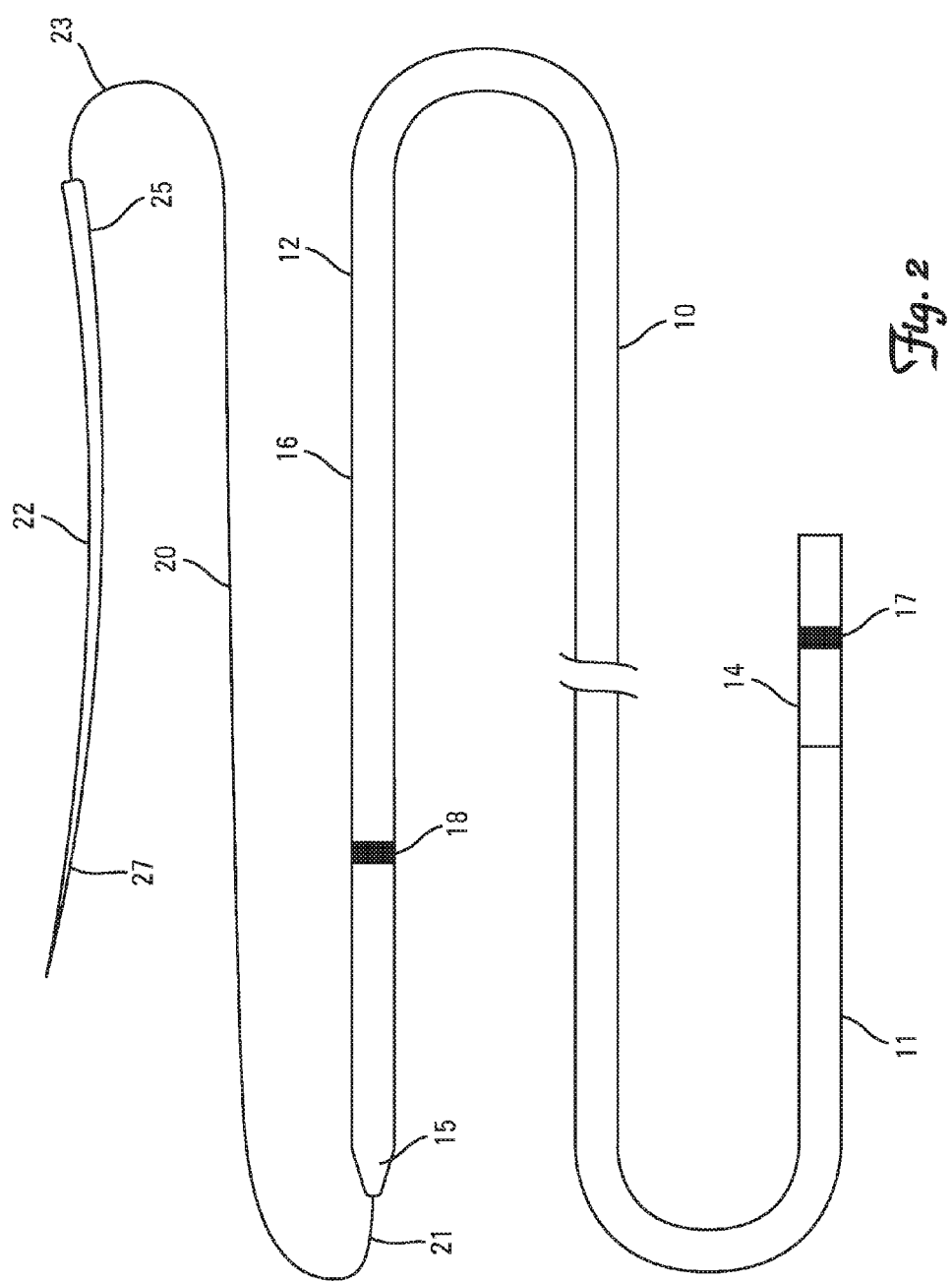

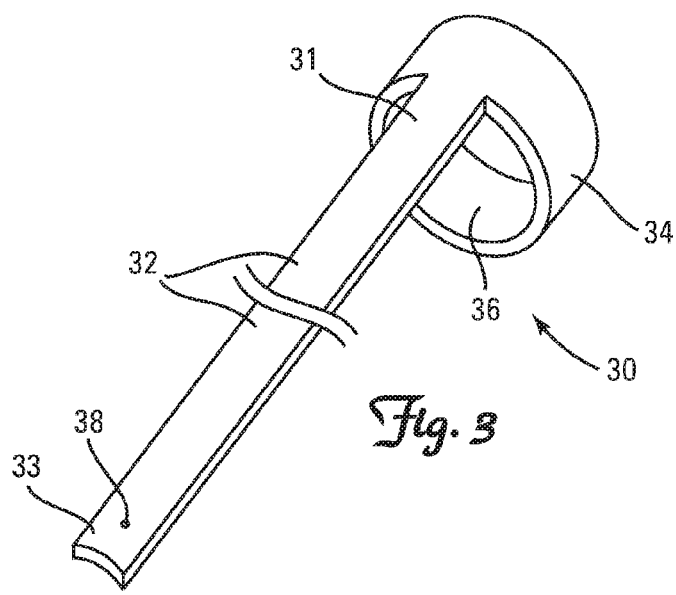
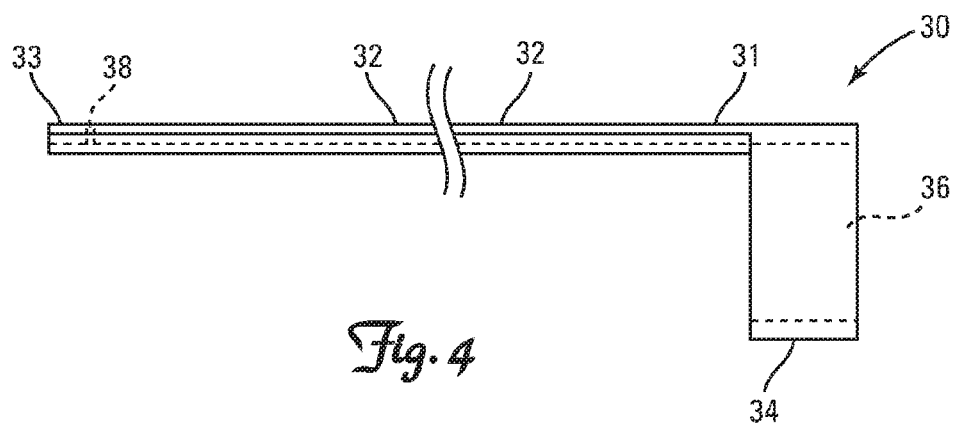
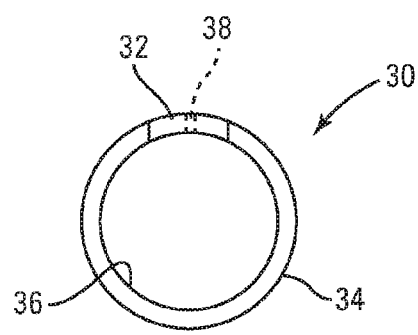

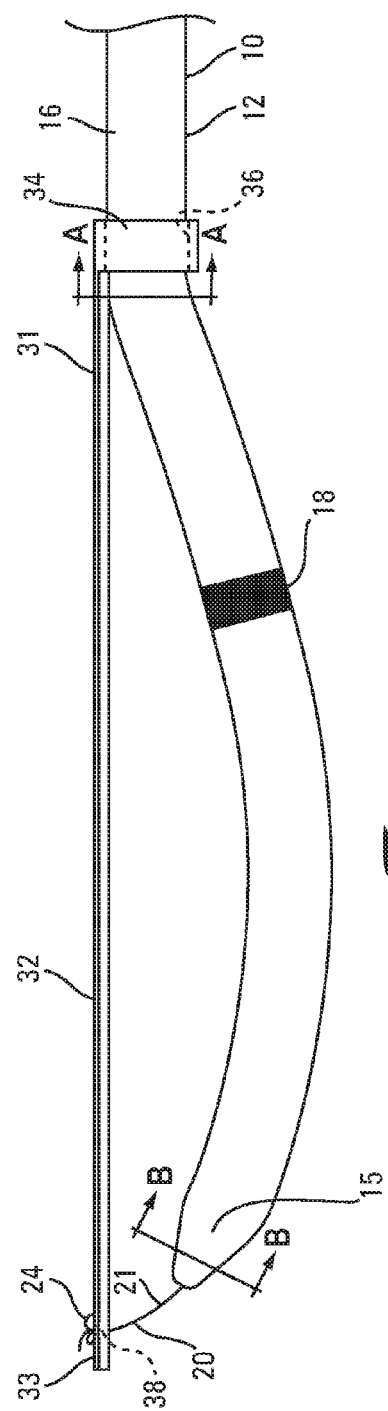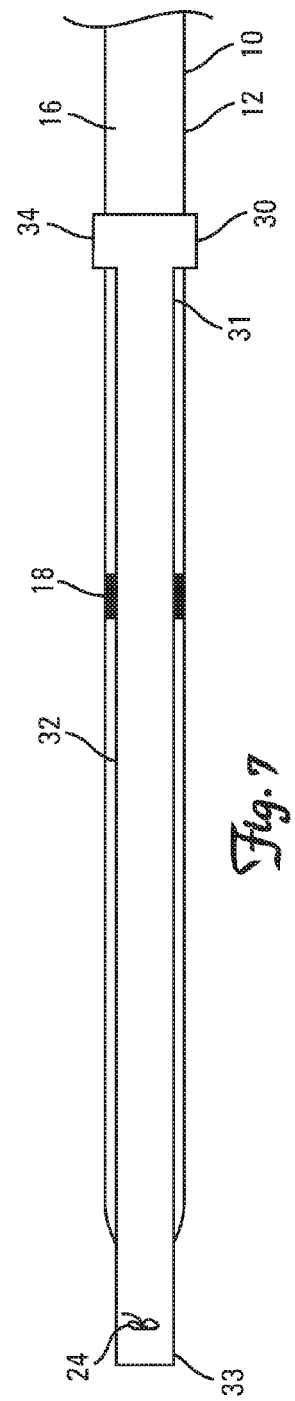

MEDICAL LEAD ANCHORING

CROSS-REFERENCE TO RELATED APPLICATION

This application claims priority to Provisional Application No. 62/094,905, filed Dec. 19, 2014, which is herein incorporated by reference in its entirety.

TECHNICAL FIELD

The present disclosure is directed to systems for stimulating anatomical structures. More particularly, the present disclosure is directed to anchoring of leads.

BACKGROUND

Implantable pulse generators have been used to stimulate a variety of anatomical structures, such as the heart, the brain, the spinal cord, vessels, and nerves, among other targets. Electrical energy is typically conveyed from the implantable pulse generator to the targeted tissue via a lead. A variety of types of leads have been developed for these purposes. In order to maintain the ability to deliver reliable chronic therapy, the lead may need to be securable within the body, such as proximate the targeted tissue. A lack of reliable anchoring can lead to an inability to stimulate targeted tissue and/or the unintended stimulation of non-targeted tissue.

SUMMARY

In example 1, a lead system comprising: an implantable lead, the lead comprising a proximal portion, a distal portion, and at least one electrode located on the distal portion; and an anchor, the anchor comprising a ring and a flange extending from the ring, the ring comprising a lumen, the anchor configured to be mounted on the lead such that the lead extends through the lumen, the ring is located proximally of the at least one electrode, and the flange extends distal of the at least one electrode.

In example 2, the lead system of example 1, further comprising a flexible tether, the tether attached to the lead, wherein the anchor is configured to anchor the lead to tissue when mounted on the lead and attached to the tether.

In example 3, the lead system of example 2, wherein the flange further comprises a hole, and wherein the anchor is configured to attach to the tether at least in part by the tether extending through the hole.

In example 4, the lead system of either of examples 2 or 3, wherein the lead, the anchor, and the tether are configured to form a loop that surrounds a section of tissue to anchor the lead to the tissue.

In example 5, the lead system of any of examples 2-4, further comprising a needle, the needle comprising a proximal portion that is attached to a distal portion of the tether.

In example 6, the lead system of example 5, wherein the flange is longer than the needle and the needle is longer than the span of the at least one electrode along the lead.

In example 7, the lead system of either of examples 5 or 6, wherein the tether is longer than the needle.

In example 8, the lead system of any of examples 1-7, wherein the lead further comprises a distal tip located on the distal portion, the distal tip distal of the at least one electrode, wherein the anchor is configured to be mounted on the lead such that the ring is over the lead at a location proximal of the at least one electrode while the flange extends distal of the distal tip.

In example 9, the lead system of example 8, wherein the distal tip comprises a lumen and the tether extends through the lumen of the distal tip.

In example 10, the lead system of any of examples 1-9, wherein the ring is slidable over the proximal portion and the distal portion of the lead.

In example 11, the lead system of any of examples 1-10, wherein the ring has a groove extending around the ring and the groove is configured to receive a suture to attach the ring to the lead.

In example 12, the lead system of any of examples 1-11, wherein the at least one electrode comprises multiple electrodes.

In example 13, the lead system of any of examples 1-12, wherein the flange is narrower than the lead.

In example 14, the lead system of any of examples 1-13, wherein the flange extends in an orthogonal orientation with respect to the ring.

In example 15, the lead system of any of examples 1-14, wherein the ring has a length in a range of about 0.0625-0.5 inches (0.16-1.27 centimeters).

In example 16, a lead system comprising: an implantable lead, the lead comprising a proximal portion, a distal portion, a distal tip located on the distal portion, and at least one electrode located on the distal portion proximal of the distal tip; and an anchor, the anchor comprising a ring and a flange extending from the ring, the ring comprising a lumen, the anchor configured to be mounted on the lead such that the lead extends through the lumen while the ring is located proximally of the at least one electrode and the flange extends distally of the distal tip.

In example 17, the lead system of example 16, further comprising a flexible tether having a proximal portion and a distal portion, the tether attached to the lead, the proximal portion of the tether extending from the distal tip of the lead, wherein the anchor is configured to anchor the lead to tissue when mounted on the lead and attached to the tether.

In example 18, the lead system of example 17, wherein the flange further comprises a hole, and wherein the anchor is configured to attach to the tether at least in part by the tether extending through the hole.

In example 19, the lead system of either of examples 17 or 18, wherein the lead, the anchor, and the tether are configured to form a loop that surrounds a section of tissue to anchor the lead to the tissue.

In example 20, the lead system of any of examples 17-19, further comprising a needle, the needle comprising a proximal portion that is attached to the distal portion of the tether.

In example 21, the lead system of example 20, wherein the flange is longer than the needle and the needle is longer than the span of the at least one electrode along the lead.

In example 22, the lead system of any of examples 16-21, wherein the ring is slidable over the proximal portion and the distal portion of the lead.

In example 23, the lead system of any of examples 16-22, wherein the ring has a groove extending around the ring and the groove is configured to receive a suture to attach the ring to the lead.

In example 24, the lead system of any of examples 16-23, wherein the at least one electrode comprises multiple electrodes.

In example 25, the lead system of any of examples 16-24, wherein the flange is narrower than the lead.

In example 26, a lead system comprising: an implantable lead, the lead comprising a proximal portion, a distal portion, and at least one electrode located on the distal portion; an anchor, the anchor comprising a ring and a flange extending from the ring, the ring comprising a lumen, the anchor configured to be mounted on the lead such that the lead extends through the lumen, the ring is located proximally of the at least one electrode, and the flange extends distal of the at least one electrode; and a tether having a proximal portion and a distal portion, the proximal portion of the tether attached to the distal portion of the lead, the tether configured to attach to the flange, wherein the lead, the anchor, and the tether are configured to form a loop that surrounds a section of tissue to anchor the lead to the tissue.

In example 27, a method of anchoring an implantable lead to tissue with an anchor, the lead comprising a distal portion, a distal tip located on the distal portion, at least one electrode located on the distal portion proximal of the distal tip, and a tether extending from the distal tip, the anchor comprising a ring and a flange extending from the ring, the method comprising: embedding the at least one electrode in the tissue; sliding the ring in the distal direction over the lead and positioning the anchor such that the flange is located above the at least one electrode and extends distally of the distal tip; and attaching the tether to a distal portion of the flange, wherein a section of the tissue is surrounded by a loop formed by the lead, the anchor, and the tether to anchor the lead to the tissue.

In example 28, the method of example 27, wherein the lead further comprises a needle having a proximal portion, the proximal portion of the needle attached to a distal portion of the tether, and wherein embedding the at least one electrode in the fascia tissue comprises: forming a tunnel through the tissue with the needle; pulling the needle out of the tunnel while stringing the tether along the tunnel; pulling the tether through the tunnel while stringing the lead along the tunnel; and cutting the tether while the at least one electrode is within the tunnel.

In example 29, the method of example 28, wherein cutting the tether further includes leaving a portion of the tether attached to the lead, and wherein attaching the tether to the distal portion of the flange comprises tying a knot in the portion of the tether.

In example 30, the method of any of examples 27-29, wherein attaching the tether to the distal portion of the flange comprises extending the tether through a hole in the distal portion of the flange.

In example 31, the method of any of examples 27-30, further comprising wrapping a suture around the ring to attach the ring to the tissue.

In example 32, the method of any of examples 27-31, further comprising: sensing at least one bioelectrical signal with the at least one electrode while the at least one electrode is within the tunnel; and based on the at least one bioelectrical signal, moving the at least one electrode within the tunnel one or both of proximally by pulling on the lead and distally by pulling on the tether.

In example 33, the method of any of examples 27-32, further comprising cutting away an excess portion of the flange based on a length of the tunnel.

In example 34, the method of any of examples 27-33, wherein an interface between the ring and the lead inhibits distal movement of the at least one electrodes within the tunnel, and wherein the attachment of the tether to the distal portion of the flange inhibits proximal movement of the at least one electrodes within the tunnel.

In example 35, the method of any of examples 27-34, wherein embedding the at least one electrode in the tissue comprises embedding the at least one electrode above tissue targeted for electrical stimulation, and wherein positioning the anchor comprises positioning the flange above the at least one electrode and opposite the tissue targeted for electrical stimulation with respect to the lead.

Any of the preceding examples can have one or more of the following dimensions. The width of the flange can be, for example, within a range of about 0.0625-0.5 inches (0.16-1.27 centimeters). The length of the flange can be, for example, within a range of about 0.25-3.00 inches (0.63-7.62 centimeters). The thickness of the flange can be, for example, within a range of about 0.015-0.075 inches (0.038-0.19 centimeters). The length of the ring can be, for example, within a range of 0.0625-0.5 inches (0.16-1.27 centimeters). The length of the flange can be several times longer than the length of the ring 34, such as at least ten times longer. The inner diameter of the lumen of the ring can be, for example, within the range of 0.01-0.1 inches (0.025-0.25 centimeters). The outer diameter of the ring can be, for example, within the range of about 0.02-0.11 inches (0.05-0.28 centimeters).

BRIEF DESCRIPTION OF THE DRAWINGS

FIG. 2 is an isometric view of the lead of FIG. 1 serially connected with a tether and a needle.

FIG. 3 is a perspective view of an anchor.

FIG. 4 is a side view of the anchor of FIG. 3.

FIG. 5 is a front view of the anchor of FIG. 3.

FIG. 6 is a side view of the anchor of FIG. 3 mounted on the lead of FIG. 2.

FIG. 7 is an overhead view of the anchor of FIG. 3 mounted on the lead of FIG. 2.

While multiple embodiments are disclosed, still other embodiments within the scope of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The present disclosure concerns leads for stimulating anatomical structures. While the carotid sinus is used as an exemplar herein for demonstrating lead features, it will be understood that lead features according to the present disclosure can be used to stimulate and/or monitor other anatomical structures. Such structures can include, but are not limited to, nerves, the heart, the spinal cord, the brain, gastrointestinal structures, pelvic structures, and the diaphragm, among others. For example, a lead according to the present disclosure may be used to stimulate the vagus nerve. In another example, a lead according to the present disclosure may be used in an epicardial application. Other applications for the leads are also contemplated as being within the scope of this disclosure.

Figure 1:
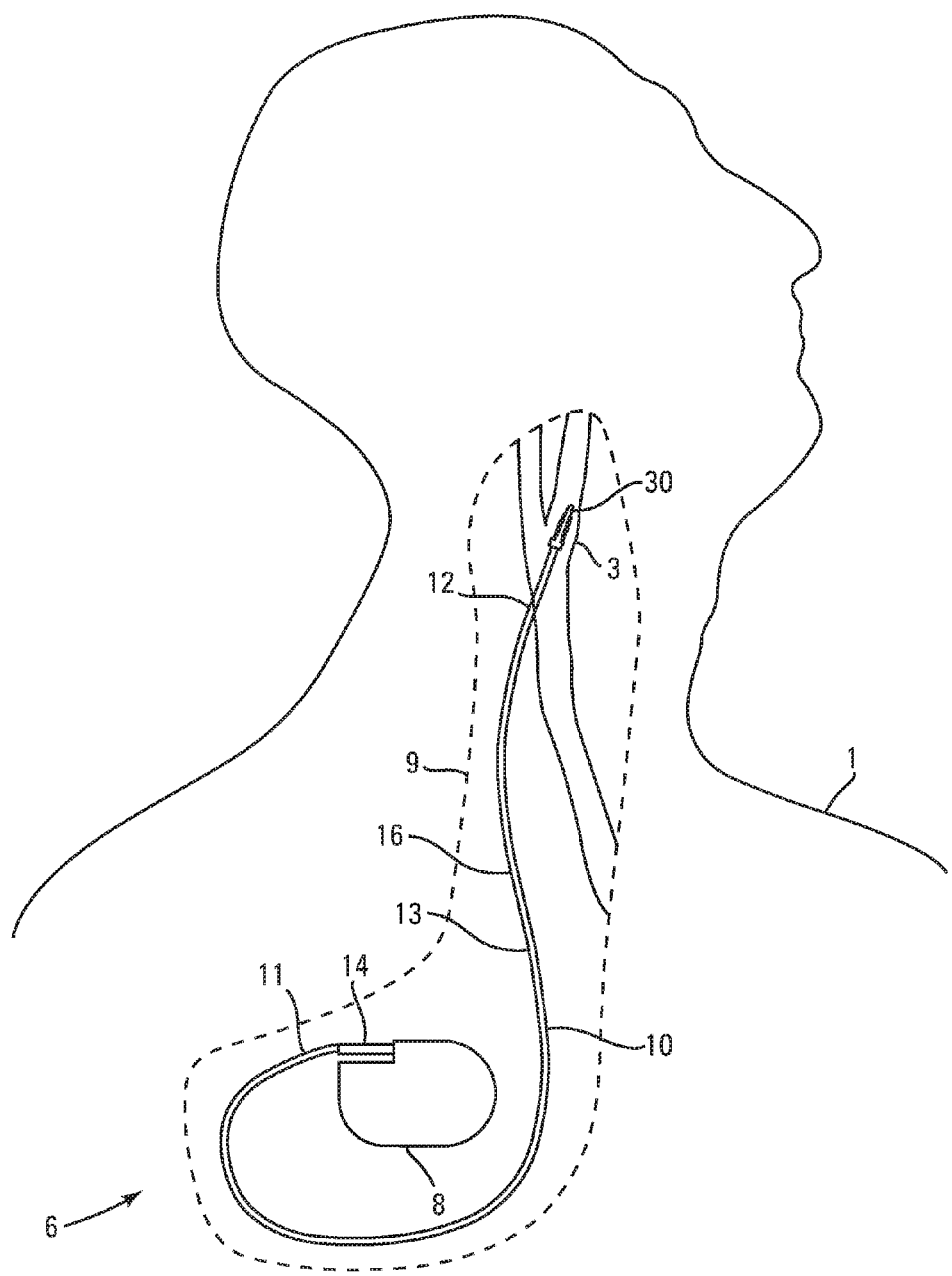
FIG. 1 is a sectional view of a system for stimulating an anatomical structure within a patient.

FIG. 1 is a sectional view of a system 6 implanted within a patient 1. The system 6 is viewable through the sectional view cutaway 9 over the patient 1. The system 6 can include an implantable pulse generator (IPG) 8. The IPG 8 can include internal circuitry configured to deliver stimulation energy, such as in the form of electrical pulses. The IPG 8 can additionally or alternatively include internal circuitry configured to sense and analyze bioelectrical signals.

The system 6 can include a lead 10. The lead 10 can comprise a proximal portion 11, a distal portion 12, and an intermediate portion 13 between the proximal portion 11 and the distal portion 12. The IPG 8 can include a receptacle for accepting a connector 14 on a proximal portion 11 of the lead 10. The lead 10 can include an elongate lead body 16 that spans from the proximal portion 11 to the distal portion 12. The lead body 16 can be formed from one or more polymeric materials, such as polyurethane and/or silicone, among other materials. The distal portion 12 of the lead 10 can be configured for mounting on the carotid sinus 3 or other tissue. Such mounting can facilitate sensing from and/or stimulating the carotid sinus 3 or other tissue. In the example of FIG. 1, the distal portion 12 of the lead 10 is anchored to the carotid sinus 3 by an anchor 30. The anchoring of the lead 10 with the anchor 30 is further discussed herein.

FIG. 2 is an isometric view of the lead 10 of FIG. 1 before implantation. As shown in FIG. 2, the lead 10 can comprise a contact 17 on the connector 14 and an electrode 18 on the distal portion 12. The connector 14 can be inserted into the receptacle of the IPG 8 to establish an electrical connection between a channel of the IPG 8 and the contact 17. One or more conductors (not illustrated) extending within the lead body 16 can conduct electrical signals between the contact 17 and the electrode 18, as is known in the art. While one contact 17 and one electrode 18 are shown in the embodiment of FIG. 2, it will be understood that other amounts of contacts and electrodes, as well as conductors electrically connecting respective sets of the contacts and electrodes, can be provided, such as two, three, four, or more of each.

The lead 10 can include a distal tip 15. The distal tip 15 shown in FIG. 2 has a tapered profile. The distal tip is narrower distally and wider proximally. The tapered profile allows the lead to be moved through tissue more easily and with less trauma as compared to a blunt profile.

As shown in FIG. 2, a tether 20 can be attached to the lead 10. The tether 20 can include a proximal portion 21 and a distal portion 23. The tether 20 is preferably formed from non-absorbable, biocompatible material. As examples, the tether 20 can be formed from nylon, polyester, polyvinylidene difluoride, or polypropylene, among other materials.

The proximal portion 21 of the tether 20 can be attached to the distal portion 12 of the lead 10. In some embodiments, the tether 20 is attached to the lead 10 by part of the proximal portion 25 of the tether 20 being embedded in polymeric material that forms the distal tip 15 of the lead 10. In some embodiments, the distal tip 15 of the lead 10 can include a lumen and part of the proximal portion 21 of the tether 20 can extend through the lumen and can be attach to an internal component of the lead 10, such as by being knotted around a metal conductor of the lead 10.

A needle 22 can be attached to the tether 20 opposite the lead 10. The needle 22 can include a proximal portion 25 and a distal portion 27. The distal portion 23 of the tether 20 can be attached to the proximal portion 25 of the needle 22. In some embodiments, the proximal portion 25 of the needle 22 can include a lumen into which the distal portion 23 of the tether 20 can extend. The proximal portion 25 of the needle 22 can be crimped or swaged around the distal portion 23 of the tether 20 within the lumen to attach the tether 20 to the needle 22. In some other embodiments, the proximal portion 25 of the needle 22 can include an eyelet to which the tether 20 can be knotted.

The distal portion 27 of the needle 22 can be sharp so as to be configured to pierce tissue. The needle 22 can be tapered from the proximal portion 25 to the distal portion 27 to minimize trauma as the needle moves through tissue. The outer diameter of the proximal portion 25 of the needle 22 can be slightly smaller than, or the same diameter as, the largest outer diameter of the distal portion 27 of the lead 10. The needle 22 can be formed from a metal, such as stainless steel. The needle 22 embodiment shown in FIG. 2 is curved. The curved shape of the needle 22 allows the distal portion 27 of the needle 22 to exit tissue while the proximal portion 25 is driven into tissue. In various other embodiments, the needle 22 can be straight.

FIG. 3 shows an isometric view of an anchor 30. The anchor 30 can include a ring 34 and a flange 32. The ring 34 includes a lumen 36. As shown in FIG. 3, the flange 32 projects from the ring 34. In the embodiment of FIG. 3, the flange 32 projects distally from the ring 34. The flange 32 can include a proximal portion 31 and a distal portion 33. The proximal portion 31 of the flange 32 can be attached to the ring 34. The flange 32 can be cantilevered so as to not connect to other parts of the anchor 30 except for the proximal portion 31 of the flange 32 connecting to the ring 34. The distal portion 33 of the flange 32 can include a hole 38. The hole 38 can be sized to accommodate the tether 20 passing there through.

The anchor 30 can be made in various ways. The anchor 30 can be molded as a single piece, such as by injection molding. In some other embodiments, the flange 32 can be formed separately from the ring 34, and these two components can be attached by an adhesive or heat bond. For example, the flange 32 may be molded while the ring 34 may also be molded, separately, or the ring 34 may be cut from an extruded tube. In some embodiments, the entirety of the anchor 30 can be formed from a tube, such as a tube having a large single lumen. A sectional portion of the tube, corresponding to the ring 34, can be left in place and a longitudinal cross-section corresponding to the flange 32 can also be left in place while the rest of the tube can be removed to form the anchor 30. For example, a bottom longitudinal section, a left side longitudinal section, and a right side longitudinal section (e.g., co-extensive with the flange 32) can each be removed from the tube to leave only the flange 32 extending of the ring 34. The hole 38 can be formed by drilling through the flange 32. The anchor 30 can be formed from a polymer material. As examples, the anchor 30 can be formed from nylon, polyester, silicone, or polyurethane, among other materials. In some embodiments, the flange 32 can be formed partially from a mesh material, such as polyethylene terephthalate, to resist tearing (e.g., from a suture).

The width of the flange 32 can be, for example, within a range of about 0.0625-0.5 inches (0.16-1.27 centimeters). The length of the flange 32 can be, for example, within a range of about 0.25-3.00 inches (0.63-7.62 centimeters). The thickness of the flange 32 can be, for example, within a range of about 0.015-0.075 inches (0.038-0.19 centimeters). The length of the ring 34 can be, for example, within a range of 0.0625-0.5 inches (0.16-1.27 centimeters). The length of the flange 32 can be several times longer than the length of the ring 34, such as at least ten times longer. The inner diameter of the lumen 36 of the ring 34 can be, for example, within the range of 0.01-0.1 inches (0.025-0.25 centimeters). The outer diameter of the ring 34 can be, for example, within the range of about 0.02-0.11 inches (0.05-0.28 centimeters).

FIG. 4 illustrates a side view of the anchor 30. The elongated profile of the flange 32 can be orientated orthogonal to the diameter of the ring 34. In some other embodiments, the flange 32 does not project orthogonally from the ring 34. For example, while the flange 32 projects at a 90° angle with respect to the ring 34, a larger angle, such as 120°, is possible. As shown in the side view of FIG. 4, the flange 32 can extend straight without bending. In this way, the flange 32 can be planar. The flange 32 can be stiff and resistant to bending (e.g., by use of a stiff material and/or by controlling the thickness of the flange 32) when implanted.

FIG. 5 is a front view of the anchor 30. As shown in FIG. 5, the front profile of the flange 32 is curved. The flange 32 can be curved in this manner from the proximal portion 31 to the distal portion 33, such as along the entire length of the flange 32. The curvature of the flange 32 can be the same as the curvature of the inner diameter and/or the outer diameter of the ring 34. The front profile of the flange 32 can alternatively be non-curved (e.g., flat).

As shown in FIGS. 3-5, the flange 32 extends along a top side of the anchor 30 but does not extend along lateral sides (e.g., left and right) nor the bottom side of the anchor 30. In other words, except for the ring 34, no other part of the anchor 30 may extend along the left side, the right side, and/or the bottom side of the anchor 30. As such, the side profile of the anchor 30 can have an "L" shape, as shown in FIG. 4.

FIG. 6 shows a side view of the anchor 30 mounted on the lead 10. The lead 10 can extend through the lumen 36 of the ring 34. The inner diameter of lumen 36 can be larger than the outer diameter of the lead body 16 to allow the lead body 16 to freely move within the lumen 36. Alternatively, the inner diameter of the lumen 36 can be dimensionally equal to the outer diameter of the lead body 16, or the inner diameter of the lumen 36 can be less than the outer diameter of the lead body 16 to create an interference coupling between the surfaces of the inner diameter of the lumen 36 and the outer diameter of the lead body 16.

As shown in the side view of the mounted arrangement of FIG. 6, the flange 32 can extend along the distal portion 12 of the lead 10. In some implementations, the flange 32 extends parallel, or substantially parallel with the distal portion 12 of the lead 10. The distal portion 33 of the flange 32 can extend distally of the distal tip 15 of the lead 10. The tether 20, extending from the distal tip 15, extends through the hole 38 in the distal portion 33 of the flange 32. As shown in the side view of FIG. 6, the distal portion 12 of the lead 10 is below the flange 32. The tether 20 extends from the underside of the flange 32, through the hole 38, and out the topside of the flange 32. The tether 20 is formed into a knot 24 on the topside of the flange 32. The knot 24 is larger than the inner diameter of the hole 38 to prevent the knot 24 from slipping below the flange 32. The tether 20 can additionally or alternatively be wrapped around the distal portion 33 of the flange 32. In at least these ways, the tether 20 can connect the distal portion 12 of the lead 10 to the distal portion 33 of the flange 32.

FIG. 7 is an overhead view of the embodiment of the anchor 30 mounted on the lead 10. As shown in FIG. 7, the distal portion 12 of the lead 10 is wider than the flange 32. In some alternative embodiments, the flange 32 may be wider than the distal portion 12 of the lead 10 such that no portion of the lead 10 would be visible distally of the ring 34 in the overhead view of FIG. 7.

Figure 8:
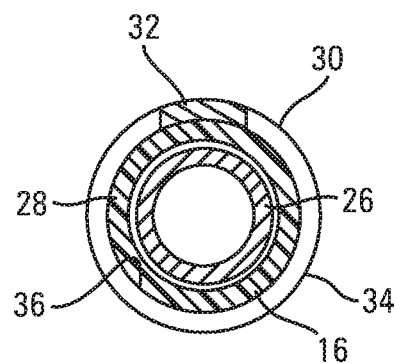
FIG. 8 is a cross sectional view along line AA of FIG. 6.

FIG. 8 is a cross-sectional view along line AA of the embodiment of FIG. 6. FIG. 8 shows that the outer diameter of the lead body 16 can be similar to the inner diameter of the lumen 36 of the ring 34. FIG. 8 also shows that the lead 10 can include a conductor 26 within the lead body 16. The conductor 26 can extend from the contact 17 to the electrode 18 (shown in FIG. 2) to electrically connect the contact 17 to the electrode 18. The conductor 26 is shown as a coil in the embodiment FIG. 8. In various other embodiments, the conductor 26 can be a cable conductor. The conductor 26 can be formed from conductive metal. While a single conductor 26 is shown in FIG. 8, multiple conductors, such as multiple coils (e.g., co-wound or wound as separate coils) and/or cable conductors can alternatively be provided within the lead body 16. Each of the conductors can electrically connect respective sets of contacts and electrodes, depending on the number of pairs of contacts and electrodes.

Figure 9:
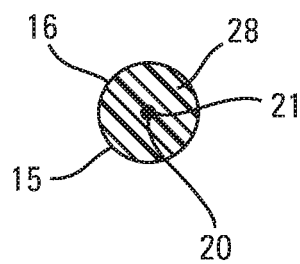
FIG. 9 is a cross sectional view along line BB of FIG. 6.

FIG. 9 is a cross-sectional view along line BB of the embodiment of FIG. 6. The cross-sectional view of FIG. 9 shows that the proximal portion 21 of the tether 20 can be embedded within polymeric material 28 of the distal tip 15. The polymeric material 28 can form other portions of the lead 10, such as the lead body 16 (shown in FIGS. 2 and 8). Although not shown, the tether 20 can wrap around (e.g., in a knot) the conductor 26 (shown in FIG. 8) to attach the tether 20 to the conductor 26 or other component of the lead 10.

FIGS. 10-16 show a sequential series of steps, from the same cross sectional view of tissue, for anchoring the lead 10. While the lead 10 and anchor 30 of FIGS. 1-9 are featured in the steps of FIGS. 10-16, is it noted that other lead and/or anchor configurations can be used with these steps and with similar steps.

Figure 10:
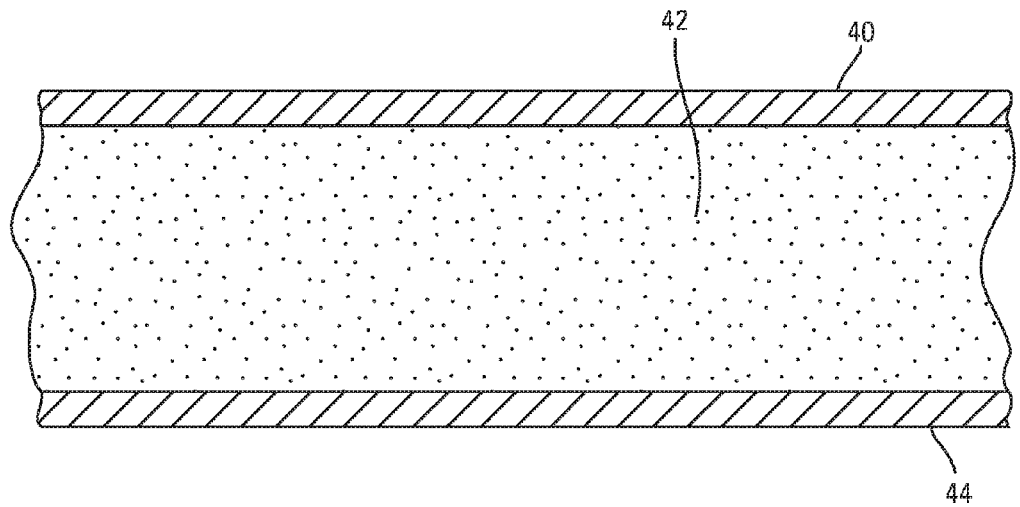
FIG. 10 is a cross sectional view of tissue at an implant site.

The tissue of FIGS. 10-16 can include targeted tissue 44. Targeted tissue 44 can be nerve tissue (e.g., the vagal nerve, baroreceptors), cardiac tissue (e.g. epicardium), muscle tissue, a vessel (e.g., the carotid sinus), and/or other tissue targeted for electrical stimulation and/or sensing. The targeted tissue 44 is shown as being underneath fascia tissue 42 in FIGS. 10-16. Fascia tissue 42 can be muscle, fat and/or connective tissue, amongst other possibilities. Surface tissue 40 can cover the fascia tissue 42, as shown in FIG. 10. Surface tissue 40 can be, for example, skin tissue or pericardial tissue.

Figure 11:
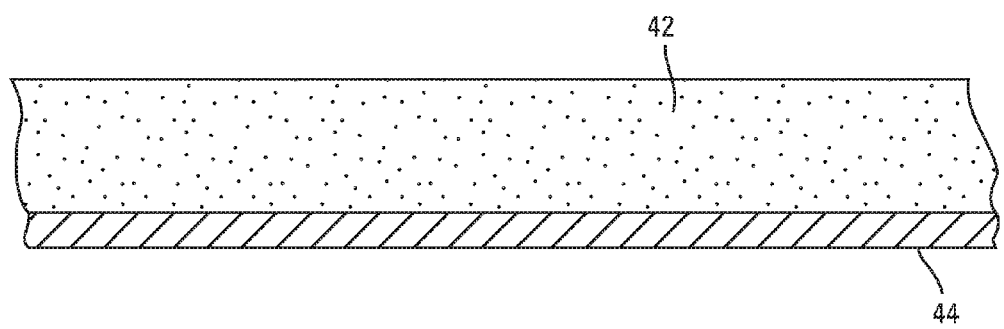
FIG. 11 is a cross sectional view of the tissue of FIG. 10 after removal of tissue layers.

FIG. 11 shows the surface tissue 40 having been excised relative to FIG. 10. FIG. 11 further shows part of the fascia tissue 42 having been excised. Removal of the surface tissue 40 and the fascia tissue 42 can be performed by known surgical techniques, such as with a scalpel. As shown in FIG. 11, the fascia tissue 42 may be only partially removed such that some fascia tissue 42 remains above the targeted tissue 44.

Figure 12:
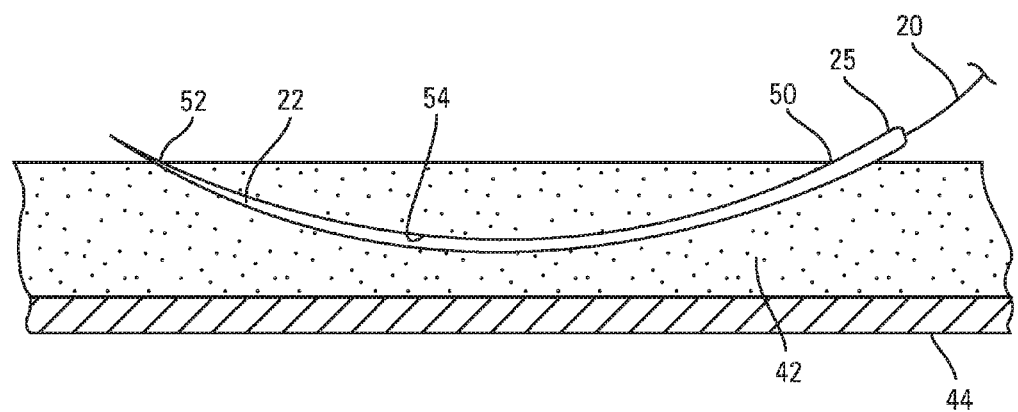
FIG. 12 is a cross sectional view of the tissue of FIG. 11 being pierced with a needle.

FIG. 12 shows the needle 22 being moved through the fascia tissue 42. The needle 22 can enter the fascia tissue 42 at an entry site 50, move along the targeted tissue 44 (e.g., 1-5 millimeters away), and exit the fascia tissue at an exit site 52. The movement of the needle 22 through the fascia tissue 42 forms a tunnel 54 between the entry site 50 and the exit site 52. The tunnel 54 can extend substantially parallel with the targeted tissue 44, particularly in cases where the targeted tissue 44 is an elongated vessel or nerve. The tunnel 54 in this example is curved, due in part to the use of a curved needle 22. In some other embodiments, the tunnel 54 can be formed to be straight, such as with a straight needle, by pressing downward on the fascia tissue 42 laterally from the entry site 50 and the exit site 52 before entry of the needle 22 and/or by pulling the fascia tissue 42, between the entry site 50 and the exit site 52, upward. It will be understood that the distance between the entry site 50 and the exit site 52 can be less than the length of the needle 22, and accordingly the length of the tunnel 54 can be less than the length of the needle 22. As shown in FIG. 12, the tether 20 can be attached to the proximal portion 25 of the needle 22 while the tunnel 54 is being formed.

Figure 13:
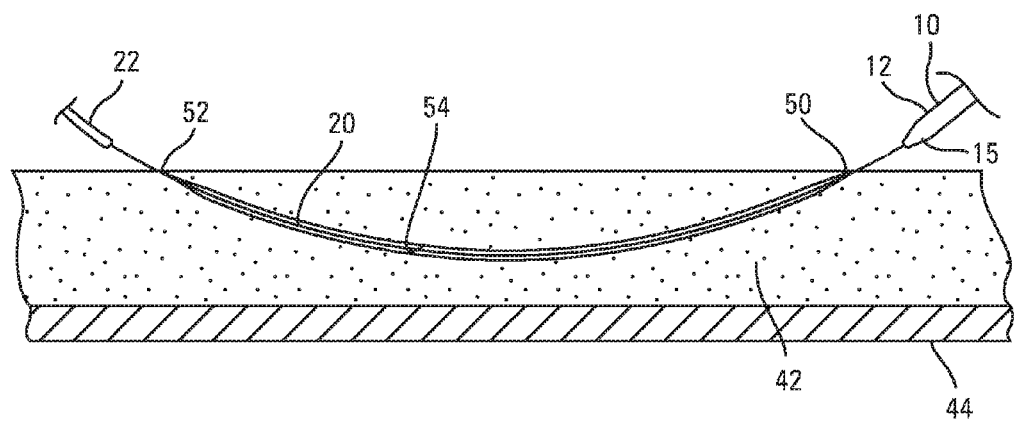
FIG. 13 is a cross sectional view of a tether being pulled by the needle into the tissue of FIG. 12.

FIG. 13 shows the needle 22 having been fully moved through the tunnel 54, exiting the fascia tissue 42 at the exit site 52. The tether 20, attached to the needle 22, can be trailed behind the needle 22 within the tunnel 54. As shown in FIG. 13, the tether 20 can be longer than the tunnel 54 such that the tether 20 can extend proximally past the entry site 50 and distally past the exit site 52.

Figure 14:
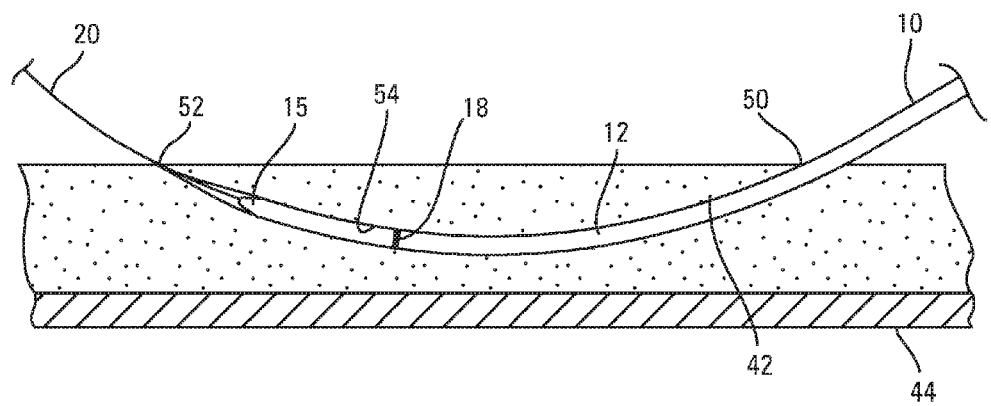
FIG. 14 is a cross sectional view of a lead being pulled by the tether into the tissue of FIG. 13.

FIG. 14 shows the distal portion 12 of the lead 10 having been moved into the tunnel 54. In some cases, the tether 20 can be pulled distally (e.g., by the surgeon grasping the tether 20 and/or the needle 22 distally of the exit site 52) to pull the distal portion 12 of the lead 10 into the tunnel 54. As shown in FIG. 14, the lead 10 can protrude proximally of the entry site 50. The electrode 18 can be embedded in the fascia tissue 42. The lead 10 of FIG. 14 only includes a single electrode 18. In embodiments where more than one electrode are provided on the lead 10, all such electrodes may be within the tunnel 54. For example, no electrodes of the lead 10 may be located proximally of the entry site 50 nor distally of the exit site 52 (excluding one or more contacts 17 on the connector 14 of the lead 10). However, not all embodiments are so limited.

As shown in FIG. 14, the distal tip 15 can be embedded in the fascia tissue 42. The tether 20 can extend through the exit site 52 and distally of the exit site 52. A surgeon can grasp the lead 10 distally of the exit site 52 and pull in the distal direction (to the left in FIG. 14) to move the lead 10 distally within the tunnel 54 to adjust the position of the electrode 18. Additionally or alternatively, the lead 10 can be grasped proximally of the entry side 50 and pulled in the proximal direction (to the right in FIG. 14) to move the lead 10 proximally within the tunnel 54 to adjust the position of the electrode 18. Such distal and proximal repositioning can be used to optimize the location of the electrode 18. Stimulation can be delivered from the electrode 18 and/or a signal can be sensed using the electrode 18 to assess the positioning of the electrode 18. Electrical stimulation can be delivered to test whether the targeted tissue 44 is captured from the location of the electrode 18. If the targeted tissue 44 is nerve or muscle tissue, then an electrical signal sensed from the electrode 18 may be indicative of the proximity of the electrode 18 to the nerve or muscle tissue.

Figure 15:
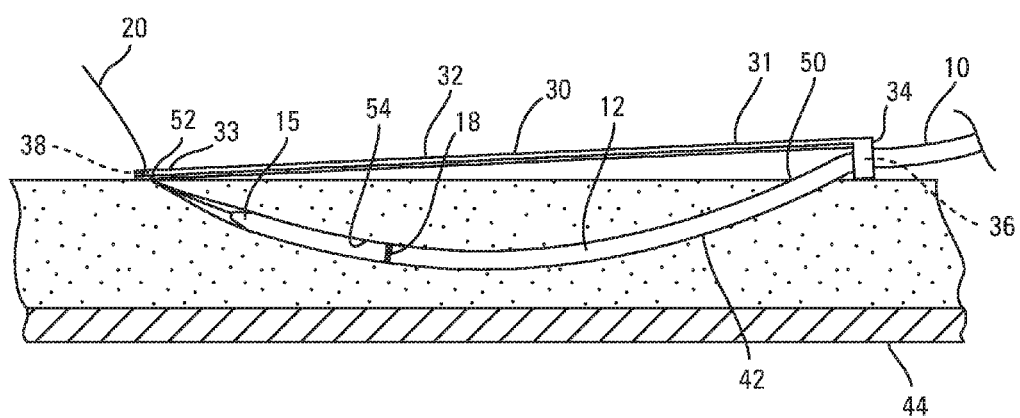
FIG. 15 is a cross sectional view of an anchor being placed over the lead of FIG. 14.

FIG. 15 shows the anchor 30 having been introduced to the implant site of the lead 10. The anchor 30 can be introduced after it is determined that the electrode 18 is in a preferred location. The anchor 30 can be slid over the proximal portion 11 of the lead 10 (shown in FIG. 2) and then slid over the distal portion 12 of the lead 10. The anchor 30 can be slid distally such that the flange 32 can be directly over the electrode 18 (and optionally over all other electrodes if additional electrodes are provided on the distal portion 12 of the lead 10) and extends distally of the distal tip 15. As further shown in FIG. 15, the tether 20 can be threaded through the hole 38 in the flange 32. The flange 32 can be longer than the distance between the entry site 50 and the exit site 52, such length allowing the flange 32 to extend distally of the distal tip 15. In some embodiments, the ring 34 can be advanced distally until the ring 34 engages the fascia tissue 42 at the entry site 50. The ring 34 can have a profile (e.g., an outer diameter) that is greater than the inner diameter of the tunnel 54 at the entry site 50 to resist entry of the ring 34 into the tunnel 54.

Figure 16:
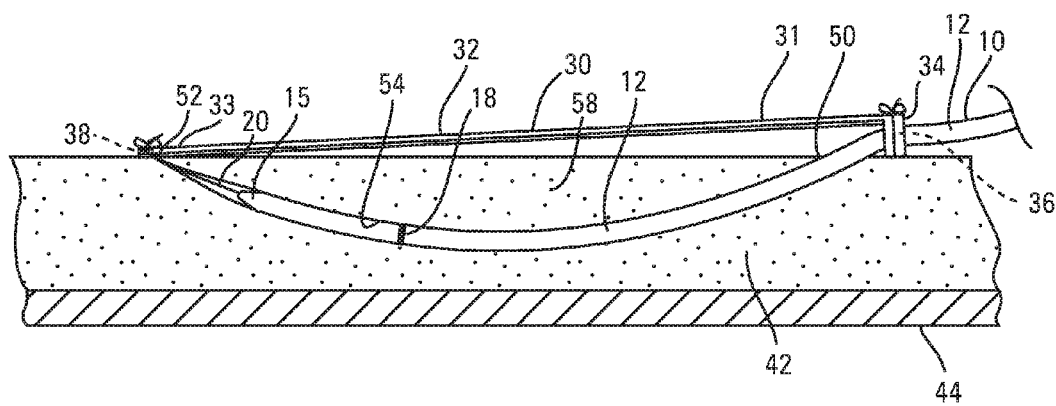
FIG. 16 is a cross sectional view of the anchor of FIG. 15 being attached to the lead of FIG. 14.

The ring 34 can be attached to the lead 10. For example, the ring 34 can be attached to the distal portion 12 of the lead 10 at a location proximal of the electrode 18. Such attachment can be accomplished in several ways. FIG. 16 shows a suture 29 having been wrapped around the ring 34 to attach the ring 34 to the lead 10. The suture 29 can be tightened around the ring 34 to tighten the ring 34 around the lead 10 and create frictional coupling between interfacing surfaces of the lead 10 and the ring 34. Alternatively, no suture may be wrapped around the ring 34. In such embodiments, the inner diameter of the ring 34 may be small enough (e.g., the same size as the outer diameter of the lead 10 or smaller than the outer diameter of the lead 10) such that frictional coupling is created between the lead 10 and the ring 34 due to the ring 34 clamping around the lead 10. It is noted that in some embodiments, the ring 34 may not be directly attached to the lead 10.

Attaching the ring 34 to the lead 10 proximal of the entry site 50 can prevent the distal portion 12 of the lead 10, and the electrode 18 in particular, from being moved distally through the tunnel 54. For example, a distally directed force (i.e. a tug) on the lead 10 distally of the exit site 52 may urge the distal portion 12 of the lead 10 to move distally within the tunnel 54, but the distal portion 12 of the lead 10 can be anchored within the tunnel 54 by the distal portion 12 of the lead 10 being attached to the ring 34, the ring 34 being outside of the tunnel 54 and too large to enter the tunnel 54 at the entry site 50.

FIG. 16 shows the tether 20 having been formed into a knot 24 above the flange 32. The knot 24 can be formed to be larger than the hole 38. Being that the flange 32 is larger than the exit site 52 of the tunnel 54, the flange 32 can prevent the distal portion 12 of the lead 10, and the electrode 18 in particular, from being moved proximally through the tunnel 54. For example, a proximally directed force (e.g., a tug) on the lead 10 proximally of the entry site 50 may urge the distal portion 12 of the lead 10 to move proximally within the tunnel 54, but the distal portion 12 of the lead 10 is anchored within the tunnel 54 by the tether 20 being attached to the lead 10 at the flange 32, the flange 32 being outside of the tunnel 54 and too large to enter the tunnel 54 at the exit site 52.

As shown in FIG. 16, a section 58 of fascia tissue 42 is surrounded by anchor 30, the lead 10, and the tether 20, which are serially connected in a loop. More specifically, the section 58 of fascia tissue 42 is bounded on the top by the flange 32 and on the bottom by the distal portion 12 of the lead 10, and further by the tether 20. This encirclement of the section 58 of fascia tissue 42 can anchor the distal portion 12 of the lead 10, and the electrode 18 in particular, to the fascia tissue 42 over the targeted tissue 44. It is noted that the section 58 of fascia tissue 42 is relatively large compared to the amount of fascia tissue 42 that would be captured by conventional suturing, wherein a relatively small volume of tissue would be surrounded by conventional sutures formed into small loops.

The anchor 30 can direct the field of stimulation energy from the electrode 18 toward the targeted tissue 44. For example, the flange 32 can be formed from electrically insulative material that resists electrical energy moving therethrough. The electrically insulative material of the flange 32 can thereby redirect electrical energy toward the targeted tissue 44. The electrically insulative material of the flange 32 can shield tissue behind the flange 32, opposite the electrode 18, from electrical stimulation. The inward curvature of the flange 32 (e.g., shown in FIGS. 5 and 8) can partially wrap around the electrode 18 to further facilitate blocking of electrical stimulation energy from reaching tissue not intended to be stimulated while redirecting the electrical stimulation energy toward the targeted tissue 44.

In some embodiments, the flange 32 has a length intended to be longer than necessary. In use, the surgeon slides the anchor 30 over the lead 10 until the ring 34 engages the fascia tissue 42 proximate the entry site 50. A portion of the flange 32 distal of the exit site 52 is then cut by the surgeon, such as with a scissors or scalpel. Before or after the cutting of the portion of the flange 32, the surgeon can cut the hole 38 through the flange 32, the hole 38 cut to be located over the exit site 52. In this way, the flange 32 may not have a pre-made hole 38. It is noted that in various embodiments, an array of holes, each similar to hole 38, is provided along the length of the flange 32 to provide the surgeon several options of pre-made holes for attaching the tether 20.

FIGS. 17-21 show various features that can be incorporated into embodiments of the present disclosure, including the embodiment show in FIGS. 2-16.

Figure 17:
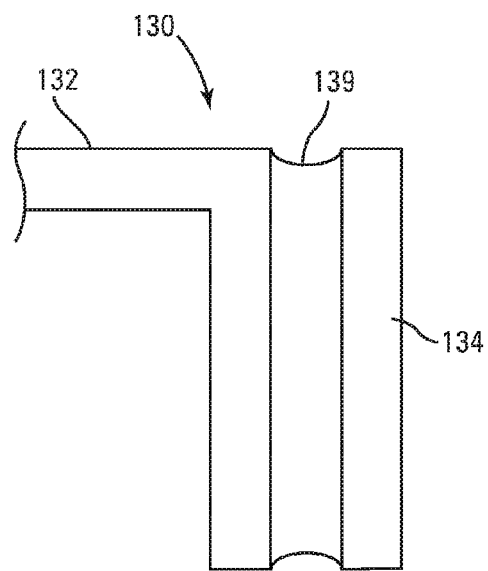
FIG. 17 is a side view of a ring of an anchor.

FIG. 17 shows a side view of an alternative embodiment of an anchor 130. The anchor 130 of FIG. 17 can be similar to any other anchor embodiment disclosed herein except where shown and/or described to be different. A ring 134 of the anchor 130 includes a suture groove 139. The suture groove 139 may extend entirely circumferentially around the ring 134, as shown, or may extend only around a portion of the ring 134. A suture may be tightened around the suture groove 139 to create frictional interference between an inner surface of the ring 134 and an outer diameter of a lead.

Figure 18:
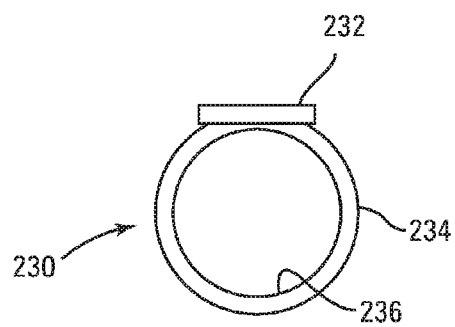
FIG. 18 is a front view of an anchor having a flat flange.

FIG. 18 is a front view of an alternative embodiment of an anchor 230. The anchor 230 of FIG. 18 can be similar to any other anchor embodiment disclosed herein except where shown and/or described to be different. The anchor 230 of FIG. 18 has a flat flange 232. The flat flange 232 of FIG. 18 may lay flat against the fascia tissue (e.g., against the relatively flat fascia tissue 42 of FIG. 15) to reduce the profile of the flange 232 at the implant site.

Figure 19:
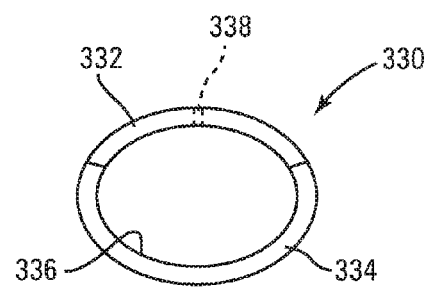
FIG. 19 is a front view of an anchor having an oval profile.

FIG. 19 is a front view of an alternative embodiment of an anchor 330. The anchor 330 of FIG. 19 can be similar to any other anchor embodiment disclosed herein except where shown and/or described to be different. In the embodiment of FIG. 19, the ring 334 of the anchor 330 has an oval profile instead of the circular profile presented herein in various other embodiments. The outer profile of a lead to be used with the anchor 330 of FIG. 19 can have an outer oval profile corresponding to the oval profile of the lumen 336 of the ring 334 of the lead 310.

Figure 20:
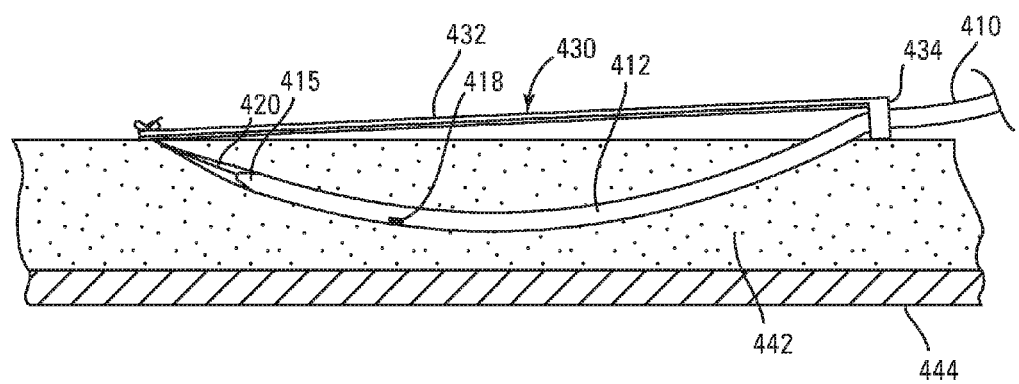
FIG. 20 is a cross sectional view of tissue in which a lead having a directional electrode has been implanted.

FIG. 20 shows a cross-sectional view of tissue of an implantation site for an alternative embodiment of a lead 410 and an anchor 430. The lead 410 and the anchor 430 of FIG. 20 can be similar to any other lead and anchor disclosed herein except where shown and/or described to be different. The implantation site can be similar to the other implantation sites referenced herein. For example, the implantation site can include targeted tissue 444 and fascia tissue 442. The lead 410 can be implanted in the fascia tissue 442 according to any technique disclosed herein and an anchor 430 may be used to anchor the lead 410 in position to stimulate targeted tissue 444. A tether 420 may extend from the lead 410 and be fastened to a flange 432. A ring 434 of the anchor 430 can extend around and engage the lead 410.

The embodiment of FIG. 20 demonstrates the use of a directional electrode 418. The directional electrode 418 may be an electrode segment (e.g., a segment of a ring, but not a full ring) or a masked electrode (e.g., a full ring electrode that is insulated on one or more sides of the electrode but exposed on one or more other sides of the electrode), among other options. As shown in FIG. 20, the directional electrode 418 faces the targeted tissue 444 to preferentially stimulate and/or sense a signal from the targeted tissue 444. In all other respects, the lead 410, the tether 420, and the anchor 430 may be the same as shown or described herein in connection with other embodiments. While a single electrode 418 is shown in the embodiment of FIG. 20, any other number of directional electrodes could be provided on the distal portion 412 of the lead 410.

Figure 21:
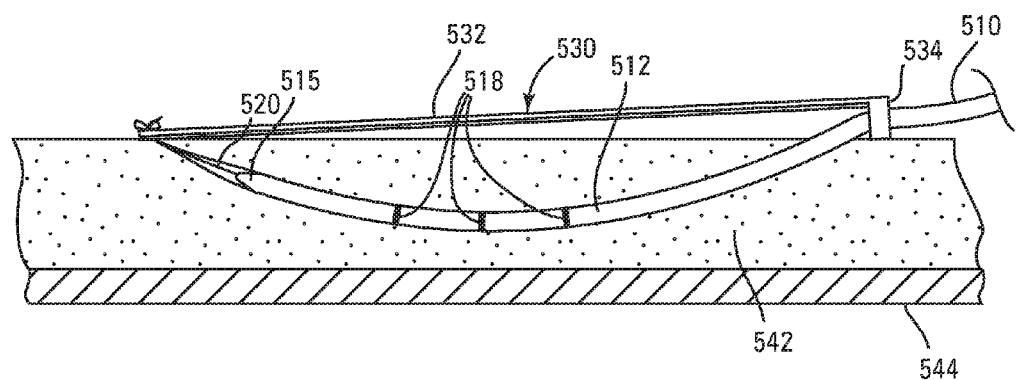
FIG. 21 is a cross sectional view of tissue in which a lead having multiple electrodes has been implanted.

While various embodiments disclosed herein include a single electrode, any embodiment can have a greater number of electrodes, such as two, three, four, or more electrodes. FIG. 21 is a side view of an alternative embodiment of a lead 510 having multiple electrodes 518. The lead 510 and/or the anchor 530 of FIG. 21 can be similar to any other lead and anchor disclosed herein except where shown and/or described to be different. The lead 510 includes three electrodes 518 on the distal portion 512 of the lead 510. In some configurations, one of the electrodes 518 can be a cathode while the other two electrodes 518 can function as anodes. While the electrodes 518 shown in FIG. 21 are ring electrodes, other types of electrodes, including directional electrodes as shown in FIG. 20, can be employed.

The implantation site shown in FIG. 21 can be similar to the other implantation sites presented herein. For example the implantation site can include targeted tissue 544 and fascia tissue 542. The lead 510 can be implanted in the fascia tissue 542 according to any technique disclosed herein and an anchor 530 may be used to anchor the lead 510 in position to stimulate targeted tissue 544. For example, a tether 520 may extend from the lead 510 and fastened to a flange 532. A ring 534 of the anchor 530 can extend around and engage the lead 510. As shown, the flange 532 is longer than the span of the electrodes 518. For example, the flange 532 extends proximally of the proximal-most electrode 518 and distally of the distal-most electrode 518. The flange 532 also extends distally of the distal tip 515 of the lead 510.

The manner of presenting illustrations and descriptions of embodiments herein is done in an exemplary format that concisely demonstrates different combinations of features. These embodiments are not to be understood as mutually exclusive, nor should the features of different embodiments be understood to be mutually exclusive. It is noted that any of the elements having similar names and/or base reference numbers can have similar characteristics even if not expressly stated. Therefore, a characteristic presented in connection with one embodiment can be applied to any other embodiment having a similar name and/or reference number, although it is noted that not all of the possible shared characteristics are identified in this manner.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

The following is claimed:

1. A lead system comprising:
    an implantable lead, the lead comprising a proximal portion, a distal portion, a distal tip located on the distal portion, and at least one electrode located on the distal portion proximal of the distal tip;
    an anchor, the anchor comprising a ring and a flange extending from the ring, the ring comprising a lumen, the anchor configured to be mounted on the lead such that the lead extends through the lumen while the ring is located proximally of the at least one electrode and the flange extends distally of the distal tip; and
    a flexible tether having a proximal portion and a distal portion, the tether attached to the lead, the proximal portion of the tether extending from the distal tip of the lead, wherein the anchor is configured to anchor the lead to tissue when mounted on the lead and attached to the tether, wherein the lead, the anchor, and the tether are configured to form a loop that surrounds a section of tissue to anchor the lead to the tissue.

2. The lead system of claim 1, wherein the flange further comprises a hole, and wherein the anchor is configured to attach to the tether at least in part by the tether extending through the hole.

3. The lead system of claim 1, further comprising a needle, the needle comprising a proximal portion that is attached to the distal portion of the tether.

4. The lead system of claim 3, wherein the flange, the needle, and the electrode each have a length, the length of the flange being longer than the length of the needle, and the length of the needle being longer than the length of the at least one electrode along the lead.

5. The lead system of claim 1, wherein the ring is slidable over the proximal portion and the distal portion of the lead.

6. The lead system of claim 1, wherein the ring has a groove extending around the ring and the groove is configured to receive a suture to attach the ring to the lead.

7. The lead system of claim 1, wherein the at least one electrode comprises multiple electrodes.

8. The lead system of claim 1, wherein the flange and the lead each have a width, and the width of the flange is narrower than the width of the lead.

9. A lead system comprising:
    an implantable lead, the lead comprising a proximal portion, a distal portion, and at least one electrode located on the distal portion;
    an anchor, the anchor comprising a ring and a flange extending from the ring, the ring comprising a lumen, the anchor configured to be mounted on the lead such that the lead extends through the lumen while the ring is located proximally of the at least one electrode and the flange extends distal of the at least one electrode; and
    a tether having a proximal portion and a distal portion, the proximal portion of the tether attached to the distal portion of the lead, the tether configured to attach to the flange, wherein the lead, the anchor, and the tether are configured to form a loop that surrounds a section of tissue to anchor the lead to the tissue.

10. A method of anchoring an implantable lead to tissue with an anchor, the lead comprising a distal portion, a distal tip located on the distal portion, at least one electrode located on the distal portion proximal of the distal tip, and a tether extending from the distal tip, the anchor comprising a ring and a flange extending from the ring, the method comprising:
    embedding the at least one electrode in the tissue;
    sliding the ring in the distal direction over the lead such that the ring is located proximally of the least one electrode and positioning the anchor such that the flange extends distally of the distal tip; and
    attaching the tether to a distal portion of the flange, wherein a section of the tissue is surrounded by a loop formed by the lead, the anchor, and the tether to anchor the lead to the tissue.

11. The method of claim 10, wherein the lead further comprises a needle having a proximal portion, the proximal portion of the needle attached to a distal portion of the tether, and wherein embedding the at least one electrode in the tissue comprises:
    forming a tunnel through the tissue with the needle;
    pulling the needle out of the tunnel while stringing the tether along the tunnel;
    pulling the tether through the tunnel while stringing the lead along the tunnel; and
    cutting the tether while the at least one electrode is within the tunnel.

12. The method of claim 11, wherein cutting the tether further includes leaving a portion of the tether attached to the lead, and wherein attaching the tether to the distal portion of the flange comprises tying a knot in the portion of the tether.

13. The method of claim 10, wherein attaching the tether to the distal portion of the flange comprises extending the tether through a hole in the distal portion of the flange.

14. The method of claim 10, further comprising wrapping a suture around the ring to attach the ring to the tissue.

15. The method of claim 10, further comprising:
    sensing at least one bioelectrical signal with the at least one electrode while the at least one electrode is within the tunnel; and
    based on the at least one bioelectrical signal, moving the at least one electrode within the tunnel one or both of proximally by pulling on the lead and distally by pulling on the tether.

16. The method of claim 10, further comprising cutting away an excess portion of the flange based on a length of the tunnel.

17. The method of claim 10, wherein an interface between the ring and the lead inhibits distal movement of the at least one electrode within the tunnel, and wherein the attachment of the tether to the distal portion of the flange inhibits proximal movement of the at least one electrode within the tunnel.

* * * * *